US00PP32335P2

(12) United States Plant Patent
Nishikawa

(10) Patent No.: US PP32,335 P2
(45) Date of Patent: Oct. 13, 2020

(54) ***BIDENS* PLANT NAMED 'FSBIDBER'**

(50) Latin Name: *Bidens triplinervia*
Varietal Denomination: FSBIDBER

(71) Applicant: Koichiro Nishikawa, Nagi-cho (JP)

(72) Inventor: Koichiro Nishikawa, Nagi-cho (JP)

( * ) Notice: Subject to any disclaimer, the term of this patent is extended or adjusted under 35 U.S.C. 154(b) by 0 days.

(21) Appl. No.: 16/602,581

(22) Filed: Nov. 4, 2019

(51) Int. Cl.
*A01H 5/02* (2018.01)
*A01H 6/14* (2018.01)

(52) U.S. Cl.
USPC ..... Plt./410

(58) Field of Classification Search
USPC ..... Plt./410
CPC ..... A01H 5/02; A01H 5/00; A01H 6/14
See application file for complete search history.

(56) References Cited

PUBLICATIONS

Danziger Blazing Embers, retrieved on Apr. 21, 2020, retrieved from the Internet at https://danzigeronline.com/variety/timeless-blazing-embers/, 5 pp. (Year: 2020).*
Greenhouse Product News 2019 Spring Trials: Top Trends, retrieved on Apr. 21, 2020, retrieved from the Internet at http://digital.gpnmag.com/i/1122703-june-2019/0?, pp. 20-23.. (Year: 2019).*

* cited by examiner

*Primary Examiner* — June Hwu
(74) *Attorney, Agent, or Firm* — Cassandra Bright

(57) ABSTRACT

A new and distinct cultivar of *Bidens* plant named 'FSBIDBER' is disclosed, characterized by a very compact plant with a mounded growth habit. Flowers are extra-large, single, and uniquely bi-color of deep orange with distinctive strong yellow coloration in the lower section of the ray florets, forming the appearance of a yellow eye. The new variety is a *Bidens*, normally produced as an outdoor garden or container plant.

2 Drawing Sheets

Figure 1:
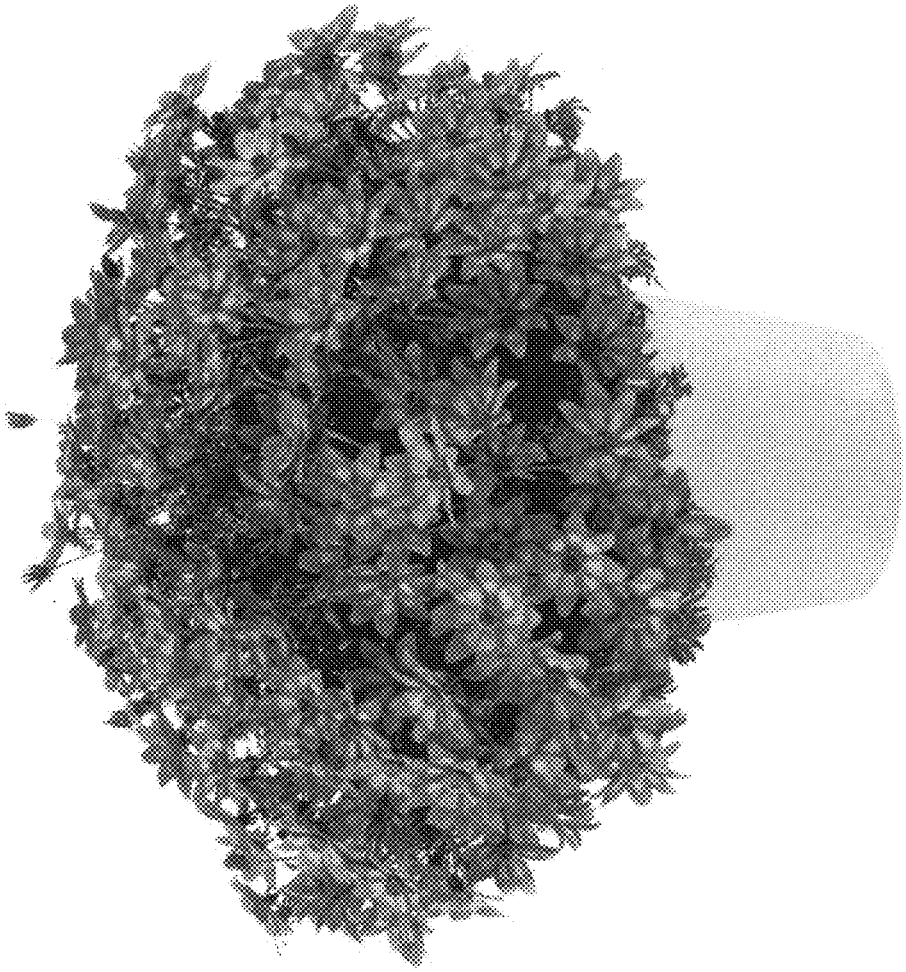

Latin name of the genus and species: *Bidens triplinervia*.
Variety denomination: 'FSBIDBER'.

BACKGROUND OF THE INVENTION

The new *Bidens* cultivar is a product of a planned breeding program conducted by the inventor, in Okayama, Japan. The crossing resulting in this new variety was made during September of 2014.

The seed parent is an unnamed, unpatented, proprietary *Bidens*. The pollen parent is a different unnamed, unpatented proprietary *Bidens*. The new variety was discovered in October of 2015 by the inventor in a group of seedlings resulting from the 2014 crossing, in a research greenhouse in Okayama, Japan.

Asexual reproduction of the new cultivar 'FSBIDBER' was first performed by terminal vegetative cuttings during October of 2015, at a research greenhouse in Okayama, Japan. Subsequent propagation by vegetative cuttings has shown that the unique features of this cultivar are stable and reproduced true to type in multiple successive generations.

SUMMARY OF THE INVENTION

The cultivar 'FSBIDBER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FSBIDBER' These 1. Ball shaped, mounded growth habit.
2. abundant flowering
3. Very compact plants.
4. Extra-large single flowers.
5. Unique bi-color flowers of deep orange with distinctive strong yellow coloration in the lower section of the ray florets, forming the appearance of a yellow eye.

PARENT COMPARISON

Plants of the new cultivar 'FSBIDBER' are similar to plants of the seed parent in most horticultural characteristics, however, plants of the new cultivar 'FSBIDBER' differ in the following;

1. The new variety has a more compact plant habit.
2. The new variety produces wider foliage.
3. The new variety flowers more abundantly than the seed parent.

Plants of the new cultivar 'FSBIDBER' are similar to plants of the pollen parent in most horticultural characteristics, however, plants of the new cultivar 'FSBIDBER' differ in the following;

1. The new variety produces a larger flower.
2. The new variety has a more vibrant flower color.

COMMERCIAL COMPARISON

Plants of the new cultivar 'FSBIDBER' can be compared to the commercial variety *Bidens* 'DANYEL9', U.S. Plant Pat. No. 20,968. These varieties are similar in most horticultural characteristics; however, 'FSBIDBER' differs in the following:

1. 'DANYEL9' has smaller flowers than the new variety.
2. 'DANYEL9' is less compact than the new variety.

3. 'DANYEL9' produces yellow flowers, the new variety is bi-color orange and yellow.

Plants of the new cultivar 'FSBIDBER' can also be compared to the unpatented commercial variety *Bidens* 'DANYEL10'. These varieties are similar in most horticultural characteristics; however, 'FSBIDBER' differs in the following:

1. 'DANYEL10' has large, semi-double flowers whereas new variety produces extra-large, single bi-color flowers.
2. 'DANYEL10' is less compact than the new variety.

Plants of the new cultivar 'FSBIDBER' can also be compared to the unpatented commercial variety *Bidens* 'Red Yellow Center'. These varieties are similar in flower color; however, 'FSBIDBER' differs in the following:

1. Plants of 'FSBIDBER' are typically 15 cm tall and about 25 cm wide, while similarly aged plants of this comparator are typically 30 to 50 cm tall and 30 to 45 cm wide.
2. Plants of the new variety are significantly more compact than plants of this comparator, which are rangier and looser.
3. Due to the plant size, shape and configuration, plants of the new variety can be grown in commercial quart sizes, whereas plants of this comparator are recommended for hanging baskets and larger pots.

BRIEF DESCRIPTION OF THE PHOTOGRAPHS

The accompanying photograph in FIG. 1 illustrates in full color a typical plant of 'FSBIDBER' grown in 13 cm pots outdoors in Moshav Mishmar Hashiva, Israel.

Figure 2:
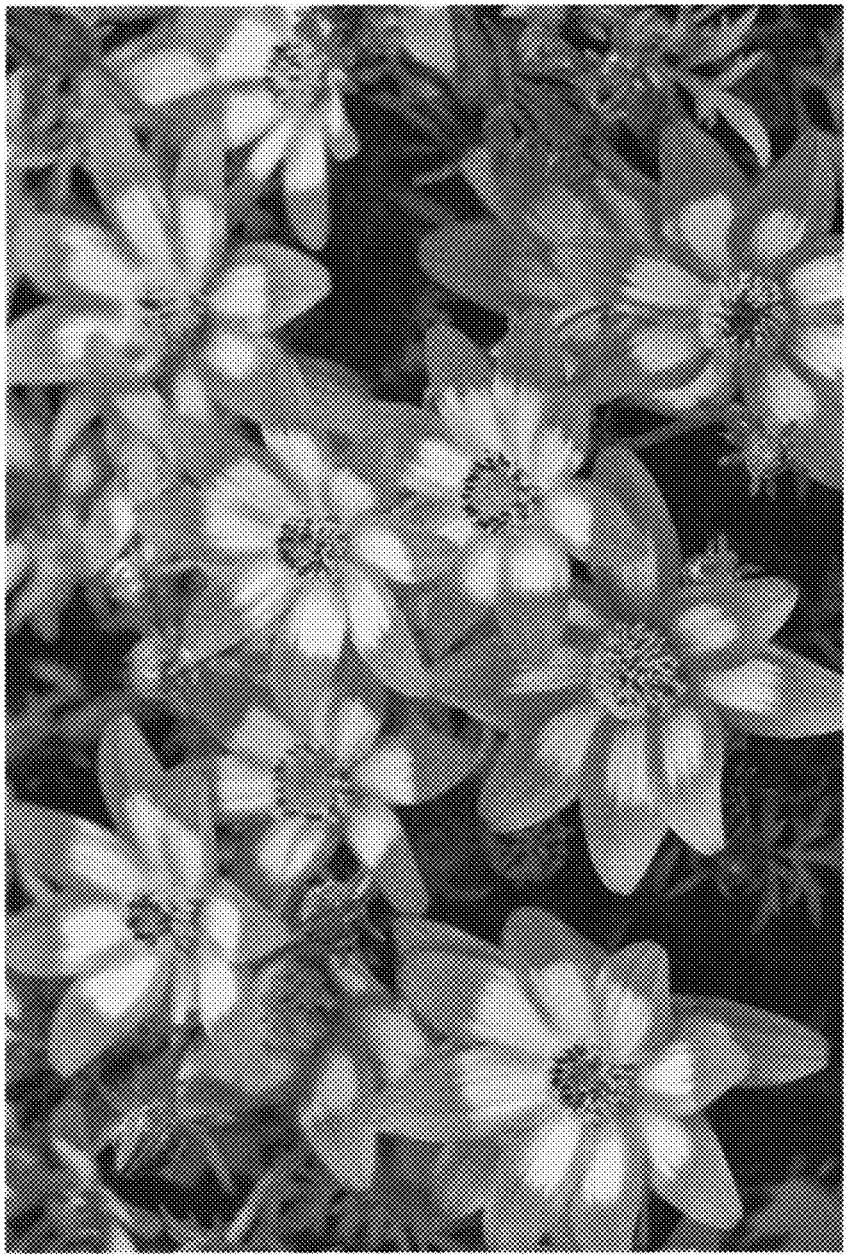

FIG. 2 illustrates in full color a close up view of a typical flower of 'FSBIDBER'. Age of the plant photographed is approximately 3 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color comparators are made to The Royal Horticultural Society Mini Colour Chart 2005 except where general terms of ordinary dictionary significance are used. The following observations and measurements describe 'FSBIDBER' plants grown in a greenhouse and outdoors in Moshav Mishmar Hashiva, Israel, under natural lighting. The plants were approximately 90 days old from a rooted cutting in a 13 cm pot. The growing temperature ranged from approximately 20° C. to 35° C. during the days, 17° C. to 23° C. during the nights. Measurements and numerical values represent averages of typical plant types. Botanical classification: *Bidens triplinervia* 'FSBIDBER'.

PROPAGATION

Time to initiate rooting: 10 to 14 days at approximately 20° C.

Root description: Fibrous. Medium brown in color, not accurately measured with R.H.S. chart.

PLANT

Growth habit: Mounded.
Height: Approximately 15 cm.
Plant spread: Approximately 25 cm.
Growth rate: Medium to slow.
Length of lateral branches: Approximately 12 cm.
Diameter of lateral branches: Approximately 0.3 cm.
Texture of lateral branches: Pubescent.
Internode length: Approximately 1 cm.
Strength of stem: Good.
Color of lateral branches: Near RHS Yellow-Green 145C.
Aspect/angle of branches: About 45°.
Number of leaves per lateral branch: Approximately 10.

FOLIAGE

Leaf:
- *Arrangement*.—Opposite.
- *Average length*.—Approximately 4 cm.
- *Average width*.—Approximately 3 cm.
- *Shape of blade*.—Overall ovate. Deeply lobed/incised, resulting in typically 7 main lobes (3 on each side 1 apical). Side lobes further segmented into 2 or 3 narrow lobes/incisions. Main lobes about 5 to 8 mm wide and about 5 to 15 mm long. Secondary lobes about 2 to 4 mm wide and 5 to 9 mm long.
- *Apex*.—Acute.
- *Base*.—Acuminate.
- *Attachment*.—Petiolate, about 45° angle from stem.
- *Margin*.—Incised.
- *Texture of top surface*.—Slightly pubescent.
- *Texture of bottom surface*.—Slightly pubescent.
- *Appearance top surface*.—Matte.
- *Appearance bottom surface*.—Matte.
- *Leaf internode length*.—Approximately 0.5 cm.
- *Color*.—Young foliage upper side: Near RHS Yellow-Green 146 A. Young foliage under side: Near RHS Yellow-Green 146 B. Mature foliage upper side: Near RHS Green N 137 B. Mature foliage under side: Near RHS Yellow-Green 147 B.

Venation:
- *Type*.—Pinnate.
- *Venation color upper side*.—Near RHS Yellow-Green 147 B.
- *Venation color under side*.—Near RHS Yellow-Green 147 A.

Petiole:
- *Length*.—About 1 cm.
- *Diameter*.—About 0.1 cm.
- *Pubescence*.—Slightly pubescent.
- *Color*.—Near RHS Yellow-Green 145 B.

FLOWER

Bloom period: Year round in Beit Dagan, Israel.

Bud:
- *Bud shape*.—Rounded.
- *Bud length*.—Approximately 1.0 cm.
- *Bud diameter*.—Approximately 0.5 cm.
- *Bud color*.—Near RHS Greyed-Orange N167 A.

Arrangement: Axillary, solitary flower.

Flower:
- *Diameter of entire flower*.—Approximately 4 cm.
- *Depth of flower*.—Approximately 1 cm.
- *Width of disc*.—Approximately 1 cm.
- *Depth of disc*.—Approximately 0.6 cm.

Ray florets:
- *Number of ray florets*.—Avg. 8.
- *Length*.—Approximately 1.5 cm.
- *Width*.—Approximately 0.8 cm.
- *Apex shape*.—Acute.
- *Margin*.—Entire.

Color:

*Ray florets*.—Upper surface at first opening: Near RHS Orange-Red 34 A, lower approximately 40% strongly blotched Yellow 15 A. Upper surface at maturity: Near RHS Greyed-Orange 169 A, lower approximately 50% strongly blotched Yellow 14 A. Upper surface at fading: Near RHS Greyed-Orange 169 C, lower approximately 50% strongly blotched Yellow 14 B. Under surface at first opening: Near RHS Greyed-Orange N167 A. Under surface at maturity: Near RHS Greyed-Orange N167 C. Under surface at fading: Near RHS Greyed-Orange N167 C.

*Disc florets*.—Number of Disc Florets: About 60. Length: Approximately 0.6 cm. Width: Approximately 0.1 cm. Shape: Linear. Margin: Entire. At first opening: Near RHS Yellow-Orange 17 A. At maturity: Near RHS Yellow-Orange 17 B. At fading: Near RHS Yellow-Orange 17 C.

Fragrance: None.

Phyllaries/involucral bracts:

*Number*.—8.

*Sepal length*.—Approximately 0.5 cm.

*Sepal width*.—Approximately 0.1 cm.

*Sepal texture*.—Slightly pubescent all surfaces.

*Apex shape*.—Acute.

*Margin*.—Entire.

*Color*.—Near RHS Yellow-Green 146 B.

Peduncle:

*Length*.—Approximately 4.0 cm.

*Diameter*.—Approximately 0.2 cm.

*Angle*.—Approximately 90°.

*Color*.—Near RHS Yellow-Green 144 B.

*Texture*.—Velvety.

REPRODUCTIVE ORGANS

Disc florets:

*Androecium*.—Stamens: 5. Anther shape: Linear. Anther length: Approximately 0.1 cm. Anther color: Near RHS Greyed-Orange 165 B. Pollen quantity: Sparse.

*Gynoecium*.—Pistil number: 1. Pistil shape: Linear. Pistil length: Approx. 0.4 cm. Style length: Approx. 0.3 cm. Style color: Near RHS Yellow-Green 154 B. Stigma shape: Two-lobed. Stigma color: Near RHS Yellow 12 B. Ovary diameter: About 0.1 cm. Ovary color: Near RHS Yellow-Green 144 C.

Ray florets: Not present.

OTHER CHARACTERISTICS

Seeds and fruits:

*Shape*.—Needle-like.

*Color*.—RHS Brown 200 A.

*Size*.—About 1 cm.

Disease/pest resistance: Neither resistance nor susceptibility to normal diseases and pests of *Bidens* has been observed.

Temperature tolerance: Temperature range from approximately 5° C. to 40° C.

Drought tolerance: Not tolerant to drought.

What is claimed is:

1. A new and distinct cultivar of *Bidens* plant named 'FSBIDBER' as herein illustrated and described.

* * * * *